United States Patent [19]

Hoehn

[11] 3,985,760

[45] Oct. 12, 1976

[54] AMINO DERIVATIVES OF 6-PHENYLISOXAZOLO[5,4-B]PYRIDINES

[75] Inventor: Hans Hoehn, Tegernheim, Germany

[73] Assignee: E. R. Squibb & Sons, Inc., Princeton, N.J.

[22] Filed: Sept. 11, 1975

[21] Appl. No.: 612,413

[52] U.S. Cl.................... 260/296 H; 260/268 BC; 260/293.58; 424/250; 424/256; 424/267
[51] Int. Cl.$^2$........................................ C07D 498/04
[58] Field of Search................ 260/268 BC, 293.58, 260/296 H

[56] References Cited
UNITED STATES PATENTS 3,755,340   8/1973   Hoehn et al.................. 260/295.5 B

*Primary Examiner*—Henry R. Jiles
*Assistant Examiner*—C. Jaisle
*Attorney, Agent, or Firm*—Lawrence S. Levinson; Merle J. Smith

[57] ABSTRACT

New amino derivatives of 6-phenylisoxazolo[5,4-b]pyridines have the general formula

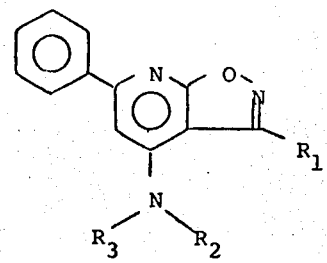

They are useful as anti-inflammatory agents.

12 Claims, No Drawings

AMINO DERIVATIVES OF 6-PHENYLISOXAZOLO[5,4-B]PYRIDINES

SUMMARY OF THE INVENTION

This invention relates to new amino derivatives of 6-phenylisoxazolo[5,4-b]pyridines. These new compounds have the general formula

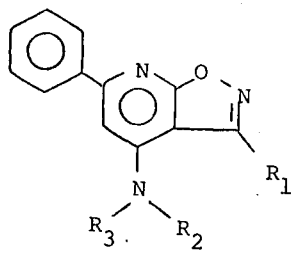

(I)

$R_1$ is hydrogen, lower alkyl or phenyl.

The basic nitrogen group

is an acyclic amino group wherein $R_2$ and $R_3$ each is hydrogen, lower alkyl, di(lower alkyl)amino(lower alkyl), phenyl, substituted phenyl, (wherein the substituent is lower alkyl, carboxy or halogen) or phenyl-lower alkyl, or $R_2$ and $R_3$ taken together with the nitrogen atom to which they are attached, form a six-membered substituted or unsubstituted saturated nitrogen heterocyclic ring which may contain a second nitrogen atom.

DETAILED DESCRIPTION OF THE INVENTION

The symbols have the following meanings in formula I and throughout this specification.

$R_1$ is hydrogen, lower alkyl or phenyl. The lower alkyl groups are straight or branched chain hydrocarbon groups having up to seven carbon atoms like methyl, ethyl, propyl, isopropyl, butyl, isobutyl, t-butyl, pentyl and the like. The $C_1$–$C_4$ lower alkyl groups and especially $C_1$–$C_2$ groups are preferred.

$R_2$ and $R_3$ each is hydrogen, lower alkyl, di(lower alkyl) amino-lower alkyl, phenyl, substituted phenyl (wherein the phenyl substituent is lower alkyl, carboxy or halogen) or phenyl-lower alkyl. The lower alkyl groups are of the same type described above and the $C_1$–$C_4$ and $C_1$–$C_2$ groups are similarly preferred. Preferably also, $R_3$ is hydrogen so that the nitrogen is monosubstituted except for lower alkyl groups wherein the

is di-lower alkylamino. The halogens include the four common halogens, but chlorine and bromine are preferred.

The

group thus forms acyclic amino groups such as amino, lower alkylamino, e.g., methylamino, ethylamino, propylamino, etc., di-lower alkylamino, e.g., dimethylamino, diethylamino, methylethylamino, dipropylamino, methylpropylamino, etc., dl(lower alkyl) amino (lower alkyl) amino, e.g., dimethylaminomethylamino, diethylaminoethylamino, dimethylaminopropylamino, etc.; phenylamino; (lower alkyl)-phenylamino, e.g., p-tolylamino, (2-ethylphenyl)amino, etc.; (carboxyphenyl)-amino, e.g., (4-carboxyphenyl)amino, (3-carboxyphenyl)amino, etc.; (halophenyl)amino, e.g., (p-chlorophenyl)amino, (o-bromophenyl)amino, etc.; or phenyl-lower alkylamino, e.g., benzylamino (which is preferred), phenethylamino, etc.

In addition, $R_2$ and $R_3$ can join together so that the

group forms a 5- or 6- membered saturated nitrogen heterocyclic which contains one or two nitrogens (in addition to carbon). The heterocyclic is unsubstituted or substituted with lower alkyl or hydroxy-lower alkyl. These heterocyclics include pyrrolidine, piperidine, (lower alkyl)piperidine, (hydroxy-lower alkyl)piperidine, piperazine, lower alkylpiperazine, (hydroxy-lower alkyl)piperazine, etc.

Preferred are those compounds wherein $R_1$ is lower alkyl, especially methyl, $R_2$ and $R_3$ each is hydrogen, lower alkyl, especially wherein the lower alkyl has up to four carbon atoms, di(lower alkyl)amino(lower alkyl), especially dimethylaminopropyl, or the cyclic amine piperazine and N-methylpiperazine. Especially preferred in this group are those compounds wherein $R_3$ is hydrogen or lower alkyl.

The new compounds of formula I are formed by the following series of reactions.

A 5-aminoisoxazole of the formula

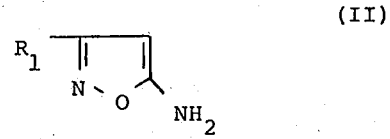

(II)

[prepared according to the procedure described in Ann. Chem. 624, 22 (1959)] is made to react with a benzoylacetic acid ester of the formula

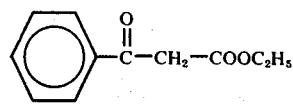

(III)

by heating at a temperature of about 130° in the presence of polyphosphorus acid, producing a compound of the formula

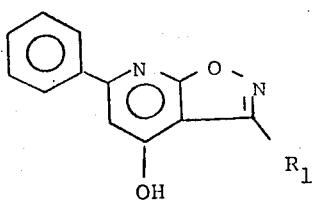

(IV)

This 4-hydroxy derivative is refluxed for several hours with a phosphorous halide like phosphorous oxychloride to obtain the intermediate of the formula

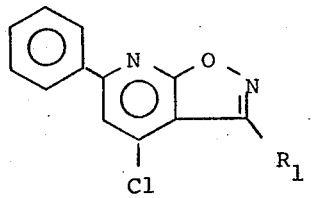

(V)

The products of formula I are then produced from the compounds of formula V by reaction with the appropriate amine of the formula

(VI)

This reaction is effected by treating the reactants in an autoclave at elevated temperatures.

Additional process details are provided in the illustrative examples.

The compounds of formula I form salts which are also part of this invention. The salts include acid-addition salts, particularly the non-toxic, physiologically acceptable members. These salts are formed by reacting the base with one or two equivalents of the inorganic or organic acid providing acid addition salts including, for example, hydrohalides (especially the hydrochloride and hydrobromide), sulfate, nitrate, phosphate, oxalate, tartrate, malate, citrate, picrate, acetate, ascorbate, succinate, arylsulfonates like benzenesulfonate, toluenesulfonate, alkanesulfonates like methanesulfonate, cyclohexanesulfamate, etc. The acid addition salts frequently provide a convenient means for isolating the product, e.g., by forming and precipitating the salt (which is not necessarily physiologically acceptable) in an appropriate medium in which the salt is insoluble, then after separation of the salt, neutralizing with a base such as barium hydroxide or sodium hydroxide, to obtain the free base.

the new compounds of this invention have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema assay in rats. The active substance is utilized in compositions such as tablets, capsules, solutions or suspensions containing up to about 300 mg. per unit of dosage of a compound or mixture of compounds of formula I or physiologically acceptable acid addition salt thereof. They are compounded in conventional manner with a physiologically acceptable vehicle or carrier, excipient, binder, preservative, stabilizer, flavor, etc. as called for by accepted pharmaceutical practice. Topical preparations containing about 0.01 to 3 percent by weight of active substance in a lotion, ointment or cream are also useful.

The following examples are illustrative of the invention and constitute preferred embodiments. They also serve as models for the preparation of other members of the group. All temperatures are in degrees celsius.

EXAMPLE 1

N-Butyl-3-methyl-6-phenylisoxazolo[5,4-b]pyridin-4-amine, hydrochloride a. 3-methyl-6-phenylisoxazolo[5,4-b]pyridin-4-ol 19.2 g. of benzoylacetic acid ethyl ester (0.1 mol.) are added dropwise to a stirred mixture of 9.8 g. of 5-amino-3-methylisoxazole (0.1 mol.) and 50 g. of polyphosphorous acid heated to 120°–125°. After the reaction has occurred, which can be recognized by changing of the color to brown, the reaction mixture is heated for an additional half hour at 125°. After the mixture has cooled to room temperature, 250 ml. of water are added in portions and stirring is continued until the compound becomes crystalline. The collected 3-methyl-6-phenylisoxazolo[5,4-b]pyridin-4-ol is washed with water, dried and recrystallized from ethanol yielding 19.9 g. (88%), m.p. 281°–282°.

b. 4-Chloro-3-methyl-6-phenylisoxazolo[5,4-b]pyridine 6.8 g. of 3-methyl-6-phenylisoxazolo[5,4-b]pyridin-4-ol (0.03 mol.) are refluxed in 60 ml. of phosphorous oxychloride for 3 hours. the excess phosphorous oxychloride is removed in vacuo and the oily residue is treated with ice water. The compound becomes solid. The compound is extracted with chloroform, washed with an aqueous sodium carbonate solution (10%) and again with water. Evaporation of the dried ($Na_2SO_4$) and charcoal treated chloroform extract provides 6.3 g. (86%) of 4-chloro-3-methyl-6-phenylisoxazolo[5,4-b]-pyridine which is recrystallized from ligroin and melts at 130°–131°.

c. N-butyl-3-methyl-6-phenylisoxazolo[5,4-b]pyridin-4-amine 12.2 g. of 4-chloro-3methyl-6-phenylisoxazolo[5,4-b]-pyridine (0.05 mol.) are added to 150 ml. of n-butylamine. The reaction mixture is heated at 150°–160° for 3 hours in an autoclave and, after cooling to room temperature, is evaported in vacuo. The residue is treated with water, filtered off and dried. 14.1 g. (100%) of N-butyl-3-methyl-6-phenylisoxazolo[5,4-b]pyridin-4-amine are recrystallized from a mixture of ligroin and ethylacetate (3:1), m.p. 126°–127°.

d. N-butyl-3-methyl-6-phenylisoxazolo[5,4-b]pyridin-4-amine, hydrochloride

To 11.8 g. of N-butyl-3-methyl-6-methyl-6-phenylisoxazolo-[5,4-]pyridin-4-amine (0.04 mol.) dissolved in 160 ml. of acetonitrile, 6.3 ml. of ethereal hydrochloric acid (255 g/l) are added. The solution is allowed to crystallize overnight to obtain 11.9 g. (93.7%) of the hydrochloride, m.p. 184°–186°.

EXAMPLE 2

N,3-Dimethyl-6-phenylisoxazolo[5,4-b]pyridin-4-amine, hydrochloride 14.7 g. 4-chloro-3-methyl-6-phenylisoxazolo[5,4-b]-pyridine (0.06 mol.) are reacted with 5.6 g. of methylamine (0.18 mol.), dissolved in 100 ml. of absolute ethanol, at 150°–160° for 3 hours in an autoclave. Then proceeding according to the procedure of Example 1c yields 14.2 g. (99%) of N, 3-dimethyl-6-phenylisoxazolo[5,4-b]pyridin-4-amine, m.p. 189°–191° (ethanol).

The hydrochloride is prepared by dissolving N, 3-dimethyl-6-phenylisoxazolo[5,4-b]pyridin-4-amine in acetonitrile and adding ethereal hydrochloric acid, yield 88.3%, m.p. 232°–234°.

EXAMPLE 3

N-[3-(Dimethylamino)propyl]-3-methyl-6-phenylisoxazolo[5,4-b]-pyridin-4-amine, hydrochloride 12.2 g. of 4-chloro-3-methyl-6-phenylisoxazolo[5,4b]-pyridine (0.05 mol.) are reacted with a solution of 15.3 g. of 3-dimethylamino-1-propylamine (0.15 mol.) in 100 ml. of absolute ethanol at 150°–160° for 3 hours in an autoclave. Work up according to the procedure of Example 1c yields 14.7 g. (95%) of N-[3-(dimethylamino)propyl]-3-methyl-6-phenylisoxazolo[5,4-b]pyridin-4-amine, m.p. 168°–169° (ethyl acetate).

The hydrochloric acid salt is formed by dissolving N-[3-(dimethylamino)peopyl]-3-methyl-6-phenylisoxazolo-[5,4-b]pyridin-4-amine in acetonitrile and adding ethereal hydrochloric acid, yield 88.3%, m.p. 230°–231°.

EXAMPLE 4

3-Methyl-4-(1-methyl-4-piperazinyl)-6-phenylisoxazolo[5,4-b]-pyridine, dihydrochloride 12.2 g. of 4-chloro-3-methyl-6-phenylisoxazolo[5,4-b]-pyridine (0.05 mol.) and a solution of 15 g. of 1-methyl-piperazine (0.15 mol.) in 100 ml. of absolute ethanol are heated at 150°–160° for 3 hours in an autoclave. Then proceeding according to the procedure of Example 1c yields 15 g. (97.5%) of 3-methyl-4-(1-methyl-4-piperazinyl)-6-phenylisoxazolo[5,4-b]-pyridine, m.p. 162°–163° (ligroin and ethyl acetate 1:1).

The dihydrochloride is prepared by dissolving 3-methyl-4-(1-methyl-4-piperazinyl)-6-phenylisoxazolo[5,4-b]pyridine in absolute ethanol and adding ethereal hydrochloric acid, yield 87.2%, m.p. 267°–268°.

The following additional products are produced by substituting 5-aminoisoxazole or another 3-$R_1$-substituted analog for the 5-amino-3-methylisoxazole in part a or the appropriate amine for butylamine in part c of Example 1, respectively:

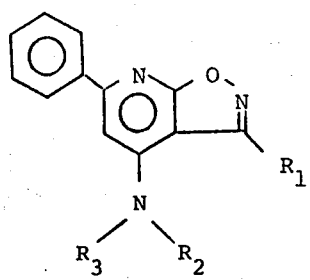

| Example | $R_1$ | $N\begin{smallmatrix}R_2\\R_3\end{smallmatrix}$ |
|---|---|---|
| 5 | H | —$NH_2$ |
| 6 | $C_2H_5$ | —N($C_2H_5$)$_2$ |
| 7 | $CH_3$ | —N($CH_3$)$_2$ |
| 8 | $CH_3$ | —N($C_5H_{11}$)$_2$ |
| 9 | $CH_3$ | —NH—$C_6H_5$ |
| 10 | H | pyrrolidinyl |
| 11 | $CH_3$ | piperidinyl |
| 12 | $CH_3$ | piperazinyl (NH) |
| 13 | $CH_3$ | NH—CH($CH_3$)—N($C_4H_9$)$_2$ |
| 14 | $CH_3$ | —$NH_2$ |
| 15 | $C_4H_9$ | —$NHC_4H_9$ |
| 16 | phenyl | —$NHCH_3$ |
| 17 | phenyl | —N($C_2H_5$)$_2$ |
| 18 | phenyl | —NH—$C_6H_5$ |
| 19 | $CH_3$ | N-(2-hydroxyethyl)piperazinyl (—N⟨⟩N$C_2H_4OH$) |
| 20 | H | —$NHCH_3$ |
| 21 | $C_2H_5$ | —NH—$C_2H_4N(C_2H_5)_2$ |

-continued

| Example | R₁ | N(R₂)(R₃) |
|---|---|---|
| 22 | H | —NHCH₂CH₂—C₆H₅ |
| 23 | CH₃ | —N(pyrrolidine) |
| 24 | H | —N(piperidine-CH₃) |
| 25 | CH₃ | —NH—C₆H₄—Cl |
| 26 | H | —NH—C₆H₄—Br |
| 27 | C₂H₅ | —NH—C₆H₄—COOH |
| 28 | CH₃ | —NH—C₆H₃(CH₃) |
| 29 | H | —NH—C₆H₄—C₂H₅ |

What is claimed is:
1. A compound of the formula

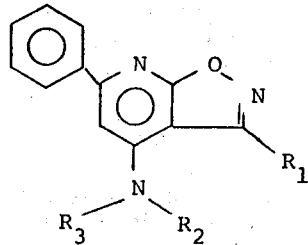

wherein R₁ is hydrogen, lower alkyl or phenyl;
R₂ and R₃ each is hydrogen, lower alkyl, di(lower alkyl)amino(lower alykl), phenyl, substituted phenyl wherein the phenyl substitutent is lower alkyl, carboxy or halogen, or phenyl-lower alkyl, or the group

is pyrrolidine, piperidine or piperazine unsubstituted or substituted with lower alkyl or hydroxy-lower alkyl; and acid addition salts thereof.

2. A compound as in claim 1 wherein R₁ is lower alkyl.

3. A compound as in claim 1 wherein R₂ is lower alkyl.

4. A compound as in claim 1 wherein R₂ is di(lower alkyl)amino(lower alkyl).

5. A compound as in claim 1 wherein R₃ is hydrogen.

6. A compound as in claim 1 wherein R₁ is lower alkyl, R₂ is lower alkyl and R₃ is hydrogen.

7. A compound as in claim 1 wherein R₁ is lower alkyl, R₂ is di(lower alkyl)amino(lower alkyl) and R₃ is hydrogen.

8. A compound as in claim 1 wherein R₁ is methyl, R₂ is n-butyl and R₃ is hydrogen.

9. Hydrochloride of the compound of claim 8.

10. A compound as in claim 1 wherein R₁ and R₂ each is methyl and R₃ is hydrogen.

11. A compound as in claim 1 wherein R₁ is methyl, R₂ is dimethylaminopropyl and R₃ is hydrogen.

12. A compound as in claim 1 wherein R₁ is lower alkyl; and R₂ and R₃ each is hydrogen, lower alkyl, di(lower alkyl)amino(lower alkyl), piperazine or N-methylpiperazine.

* * * * *